(12) United States Patent
Callison et al.

(10) Patent No.: US 11,357,501 B2
(45) Date of Patent: *Jun. 14, 2022

(54) BRAIDED FILAMENT HAVING FLAT MORPHOLOGY AND METHODS OF MANUFACTURE AND USE

(71) Applicant: Stryker Corporation, Kalamazoo, MI (US)

(72) Inventors: Ross Callison, Denver, CO (US); Kyle Craig Pilgeram, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/078,634

(22) Filed: Oct. 23, 2020

(65) Prior Publication Data

US 2021/0038220 A1 Feb. 11, 2021

Related U.S. Application Data

(63) Continuation of application No. 16/411,827, filed on May 14, 2019, now Pat. No. 10,820,901, which is a continuation of application No. 15/065,425, filed on Mar. 9, 2016, now Pat. No. 10,323,342.

(60) Provisional application No. 62/177,533, filed on Mar. 16, 2015.

(51) Int. Cl.
| | |
|---|---|
| *A61B 17/06* | (2006.01) |
| *D03D 3/00* | (2006.01) |
| *D04C 1/12* | (2006.01) |
| *D03D 15/46* | (2021.01) |

(52) U.S. Cl.
CPC ....... *A61B 17/06166* (2013.01); *D03D 3/005* (2013.01); *D03D 15/46* (2021.01); *D04C 1/12* (2013.01); *A61B 2017/06176* (2013.01); *D10B 2509/04* (2013.01)

(58) Field of Classification Search
CPC .... A61B 17/06168; A61B 2017/06176; D03D 3/005; D03D 15/46; D04C 1/12; D10B 2509/04
See application file for complete search history.

(56) References Cited

U.S. PATENT DOCUMENTS

| | | | |
|---|---|---|---|
| 2,441,601 | A | 5/1948 | Shelby |
| 3,129,631 | A | 4/1964 | Hill |
| 3,730,821 | A | 5/1973 | Jackson |
| 3,926,194 | A | 12/1975 | Greenberg et al. |
| 3,949,755 | A | 4/1976 | Vauquois |
| 4,034,763 | A | 7/1977 | Frazier |
| 4,510,934 | A | 4/1985 | Batra |
| 4,792,336 | A | 12/1988 | Hlavacek et al. |
| 4,806,737 | A | 2/1989 | Coates |
| 4,832,025 | A | 5/1989 | Coates |
| 5,007,922 | A | 4/1991 | Chen et al. |
| 5,226,336 | A | 7/1993 | Coates |
| 5,250,247 | A | 10/1993 | Chesterfield et al. |
| 5,314,446 | A | 5/1994 | Hunter et al. |

(Continued)

*Primary Examiner* — Cephia D Toomer
(74) *Attorney, Agent, or Firm* — Lerner, David, Littenberg, Krumholz & Mentlik, LLP

(57) ABSTRACT

A braided filamentary device, in one embodiment, includes a substantially flat morphology having a length, a width, and a height, and a pick count of at least about 50 picks per inch. The filamentary device is adapted to maintain its width while under a tension.

20 Claims, 5 Drawing Sheets

(56) References Cited

U.S. PATENT DOCUMENTS

| | | |
|---|---|---|
| 5,318,575 A | 6/1994 | Chesterfield et al. |
| 5,452,636 A | 9/1995 | Rattan |
| 5,454,834 A | 10/1995 | Boebel et al. |
| 5,456,722 A | 10/1995 | McLeod et al. |
| 5,478,216 A | 12/1995 | Neward |
| 5,540,703 A | 7/1996 | Barker, Jr. et al. |
| 5,645,568 A | 7/1997 | Chervitz et al. |
| 5,726,422 A | 3/1998 | Haase et al. |
| 5,792,181 A | 8/1998 | Haase et al. |
| 5,813,303 A | 9/1998 | Haase et al. |
| 5,829,979 A | 11/1998 | Kobashigawa et al. |
| 5,855,156 A | 1/1999 | Haase et al. |
| 5,891,166 A | 4/1999 | Schervinsky |
| 5,975,876 A | 11/1999 | Haase et al. |
| 6,001,121 A | 12/1999 | Haase et al. |
| 6,035,751 A | 3/2000 | Haase et al. |
| 6,045,571 A | 4/2000 | Hill et al. |
| 6,053,086 A | 4/2000 | Smyth |
| 6,309,202 B1 | 10/2001 | Demarest et al. |
| 6,319,445 B1 | 11/2001 | Haase et al. |
| 6,716,234 B2 | 4/2004 | Grafton et al. |
| 6,994,719 B2 | 2/2006 | Grafton |
| 7,029,490 B2 | 4/2006 | Grafton et al. |
| 7,892,256 B2 | 2/2011 | Grafton et al. |
| 8,012,172 B2 | 9/2011 | Grafton et al. |
| 8,088,146 B2 | 1/2012 | Wert et al. |
| 8,222,564 B2 | 7/2012 | Maiorino et al. |
| 8,672,966 B2 | 3/2014 | Wert et al. |
| 10,820,901 B2 * | 11/2020 | Callison ............ A61B 17/06166 |
| 2005/0119696 A1 | 6/2005 | Walters et al. |
| 2009/0275974 A1 | 11/2009 | Marchand et al. |
| 2012/0272816 A1 * | 11/2012 | Ueda ...................... D07B 1/025 87/8 |
| 2013/0131722 A1 | 5/2013 | Marchand et al. |
| 2014/0330299 A1 | 11/2014 | Rosenbluth et al. |
| 2016/0144066 A1 | 5/2016 | Long |

* cited by examiner

BRAIDED FILAMENT HAVING FLAT MORPHOLOGY AND METHODS OF MANUFACTURE AND USE

CROSS-REFERENCE TO RELATED APPLICATIONS

This application is a continuation of U.S. patent application Ser. No. 16/411,827, filed May 14, 2019, which is a continuation of U.S. patent application Ser. No. 15/065,425, filed on Mar. 9, 2016, and claims the benefit of the filing date of U.S. Provisional Patent Application No. 62/177,533 filed on Mar. 16, 2015, the disclosures of which are each hereby incorporated herein by reference.

BACKGROUND OF THE INVENTION

Sutures are available in a variety of materials, shapes and sizes. One such shape is a "flat" filament, where a plurality of fibers are braided such that the resulting filament is significantly wider than it is tall, resulting in a flat, or planar shape. Such sutures or filaments can be useful, for example, in increasing the contact surface area between the suture and the underlying soft tissue to help increase the contact footprint of the soft tissue against the underlying bone. This is particularly useful in, for example, rotator cuff repairs where a "suture bridge" is formed over the upper surface of the cuff to compress the cuff tissue to the underlying bone. Another advantage of such flat sutures is that the larger surface area distributes forces exerted on the tissue by the suture such that there is less of a chance the suture will cut into the tissue relative to a thinner suture (e.g., a traditional round suture).

Current flat filaments on the market, however, suffer from multiple drawbacks such that surgeons have been slow to utilize them. For example, upon applying tension to such flat filaments, the filament tends to fold onto itself (i.e., across its width) such that its entire surface area is not utilized (i.e., the entirety of the surface area, defined by its width, is not utilized). This folding-over action results in a contact surface area that is generally the same as a traditional round suture. Also, known flat filaments tend to fray or pull apart easily, particularly when being manipulated by an instrument, or the like. As such, the structural integrity of the filament is compromised.

BRIEF SUMMARY OF THE INVENTION

One benefit of the present invention is to provide a filament having a flat morphology that maintains a flat shape even under tension such that the filament does not fold onto itself across its width. As such, the filament maintains the added surface area the flat filament provides against the underlying tissue or other structure. In one embodiment, the flat morphology of the present invention is obtained by braiding a tighter weave having a higher pick count than sutures known in the art.

In one embodiment, the present invention includes a braided filamentary device including a flat morphology having a length and a width, the width being between about 0.7 mm and about 3.0 mm, and a pick count of at least about 50 picks per inch, wherein the device is capable of maintaining its flat shape when under tension. In one variation, the width can be about 1.2 mm and the pick count can be between about 60 and about 100 picks per inch. Preferably, the pick count may be about 75 picks per inch. In another variation, the width can be between about 1.7 mm and about 2.5 mm, and the pick count can be between about 50 and about 100 picks per inch. Preferably, the pick count may be about 70 picks per inch.

Further as to this embodiment, at least a portion of the device may be positioned through a filamentary fixation device. Also, at least a portion of the device may include a varying cross-sectional shape. For example, the varying cross-sectional shape can be round or oval.

Additionally as to this embodiment, the braided filamentary device can include a plurality of fibers. Moreover, at least one of the fibers of the device may have a contrasting color from the other fibers. Also, the plurality of fibers can be composed of Ultra High Molecular Weight Polyethylene (UHMWPE). Alternatively, at least one of the fibers can be composed of polyester and the other fibers are composed of UHMWPE. In another alternative, at least one of the fibers can be composed of polypropylene and the other fibers are composed of UHMWPE. In still another alternative, at least one of the fibers can be composed of silk and the other fibers are composed of UHMWPE. In a further alternative, at least one of the fibers can be composed of nylon and the other fibers are composed of UHMWPE.

In another embodiment, the present invention is a braided filamentary device, comprising a flat morphology having a length and a width, the width being between about 0.9 mm and about 2.5 mm, and a pick count between about 50 and about 100 picks per inch, wherein the filamentary device is adapted to maintain the width of between about 0.9 mm and about 2.5 mm even when under a tension, said tension generating a force along the length of the filamentary device of at least 35 Newtons. Preferably, the pick count can be about 70 picks per inch.

Further, the braided filamentary device can include a plurality of fibers. Moreover, at least one of the fibers of the device can have a contrasting color from the other fibers. Also, at least one of the fibers can be composed of polyester, or other polymer or fiber material as desired, and the other fibers are composed of UHMWPE.

In yet another embodiment, a braided filamentary device includes a substantially flat morphology having a length and a ratio of a height and a width along at least a portion of the length, wherein the ratio is between about 4.0 and about 5.5. The device may also include a pick count of at least about 50 picks per inch, and further, can be about 60 to about 80 picks per inch. Further, in one alternative example, the ratio may be between about 4.0 and about 4.5, and the pick count can be about 75. In another alternative example, the ratio can be about 5.0 and the pick count can be about 70.

DETAILED DESCRIPTION

The braided filament of the present invention has a substantially flat morphology, meaning that the shape of the filament is generally flat or planar, with a generally rectangular cross-section. The terms "substantially" and "generally" are used herein as a qualification. For example, such terms may qualify that, since the filament is a soft, braided material that is easily bent, twisted, compressed, etc., the overall shape is flat, though at certain locations along the length of the filament the shape of the filament may be slightly different from flat or planar—thus, the shape of the filament is substantially or generally flat or planar.

Figure 1:
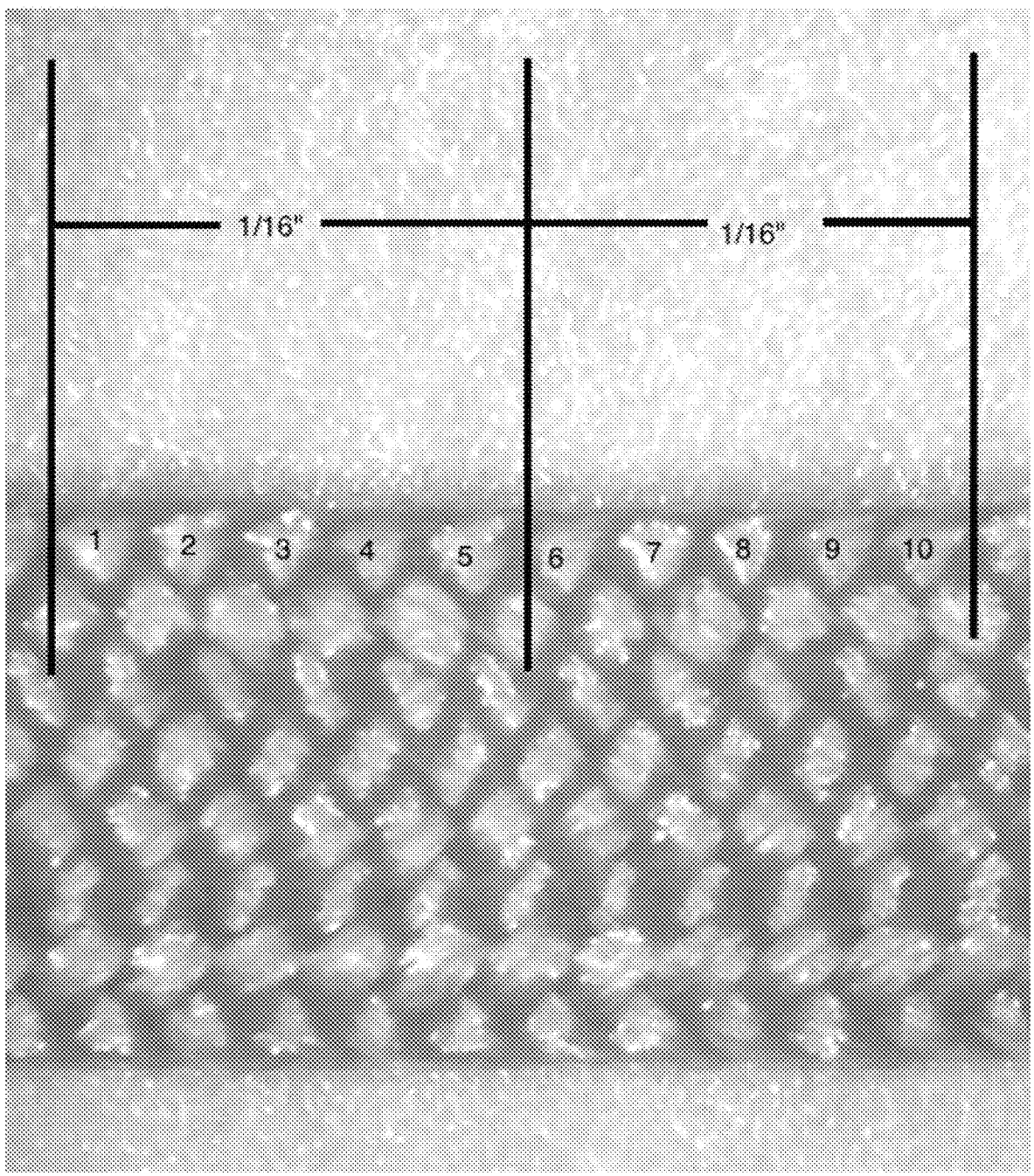
FIG. 1 illustrates one embodiment of the present invention providing an example of how a pick count is determined.
Figure 2A:
FIG. 2A illustrates a suture tape known in the art that folds over on itself when under tension.
Figure 2B:
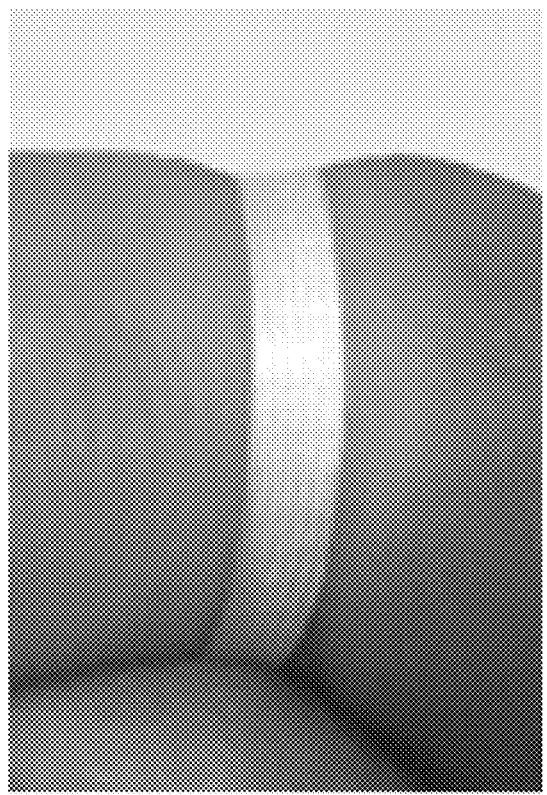
FIG. 2B illustrates one embodiments of the present invention, shown to maintain its flat morphology under tension.

In one embodiment, illustrated in FIGS. 1 and 2B, the filament of the present invention has a flat morphology, meaning the filament is woven from a plurality of fibers into a planer, flat shape. In other words, this flat filament is preferably a single layer braided structure where the fibers are woven into a flat "sheet" of material to form the flat filament, or "tape." Such tapes could also include multiple "sheets" of material on top of one another, or a single sheet folded onto itself at least once, such as the double-thickness embodiments discussed herein with an optional hollow interior in between two sheets.

As used herein, the 'pick count" is determined as illustrated in FIG. 1. To use the example of FIG. 1, every ¹/₁₆ of an inch of the braided filament includes five passes of a single fiber. Each pass is referred to as a "pick," such that for every inch, this particular filament has about 80 picks. In other words, this exemplary braided filament is woven to have 80 picks per inch, or a pick count of 80.

In one embodiment, a braided filament of the present invention has at least about 50 picks, and further may be between about 50 and about 120 picks per inch. For a smaller filament, such as one having a width of about 0.9 millimeters (mm) to about 2.0 mm, or preferably about 1.2 mm, the pick count may be between about 60 and about 100, and preferably about 65 to about 85, and more preferably about 75. For a larger filament, such as one having a width of about 1.7 mm to about 3.0 mm, or preferably about 1.7 mm to about 2.5 mm, the pick count may be between about 50 and about 100, preferably about 60 to about 80, and more preferably about 70. As discussed below, the smaller filaments may be used, for example, for labral repair, while the larger filaments may be used, for example, as a "suture bridge" in a rotator cuff repair as known in the art.

Further as to the embodiment of FIGS. 1 and 2B, the single "sheet" or layer of braided material also results in a thinner suture structure than traditional sutures in the art. For example, the height of such a braided filament may be between about 0.2 mm and about 0.4 mm, preferably between about 0.28 mm and about 0.38 mm. In one specific example, the about 1.2 mm wide filament may have a height of about 0.28 mm. In another specific example, the about 1.9 mm wide filament may have a height of about 0.38 mm. Further, these width and height dimensions can be in a ratio of at least 4.0, and further such a ratio may be between about 4.0 to about 9.0, and still further such a ratio may be between about 4.0 and about 5.5. For instance, the filament that is 1.2 mm wide and 0.28 mm in height has a ratio of about 4.3, while the 1.9 mm wide and 0.38 mm high filament has a ratio of about 5.0. In a further example, a filament that is 1.9 mm wide and 0.23 mm high has a ratio of about 8.3. Such wider and thinner braided filaments may have various benefits over traditional suture. For example, such a width to height ratio may, while providing a relatively wide surface area for contact with tissue, also can allow for better knot tying since the thinner structure, along with any compression of the filament, might provide for a tighter, and thus stronger, knot structure. The fibers forming the filament of the present invention are preferably Ultra High Molecular Weight Polyethylene (UHMWPE). Alternatively, at least one of the fibers may be composed of polyester and the other fibers are composed of UHMWPE. In another alternative, at least one of the fibers may be composed of polypropylene and the other fibers are composed of UHMWPE. In still another alternative, at least one of the fibers may be composed of silk and the other fibers are composed of UHMWPE. In yet a further alternative, at least one of the fibers may be composed of nylon and the other fibers are composed of UHMWPE. Other materials and combinations of fibers are also envisioned, as are various coatings and/or integrated materials including, for example, polytetrafluoroethylene (PTFE), collagen, bioactive materials (bioactive glass, calcium salts, etc.), or the like.

In yet another embodiment, the filament may include a color contrast, pattern or other marking along at least a portion of the length of the filament. Preferably, the marking is easily seen by a user, such as a surgeon, such that the user can identify the specific filament being used. For example, at least one fiber of polyester, or other material, incorporated in the filament may include a color or pattern contrasting from the other fibers, which may be UHMWPE. Alternatively, colored varieties of UHMWPE have recently become available and as such markings and patterns can be established in filaments made entirely of UHMWPE fibers by using a combination of different colored UHMWPE. All of the figures of this application illustrate some form of marking, with FIGS. 6A and 6B providing examples of varying markings.

Figure 6A:
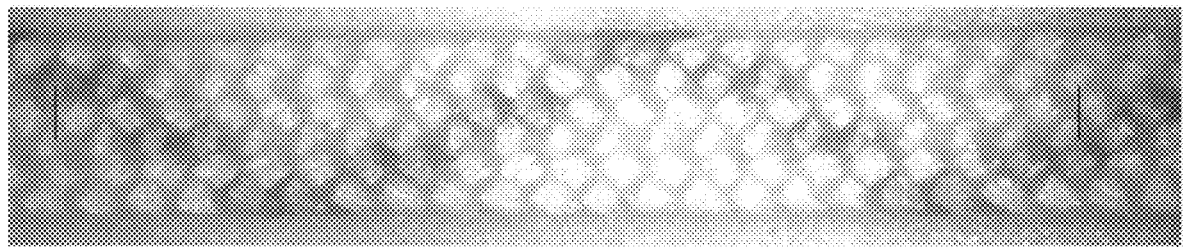
FIG. 6A illustrates an exemplary wave pattern extending along at least part of the length of the filament.
Figure 6B:
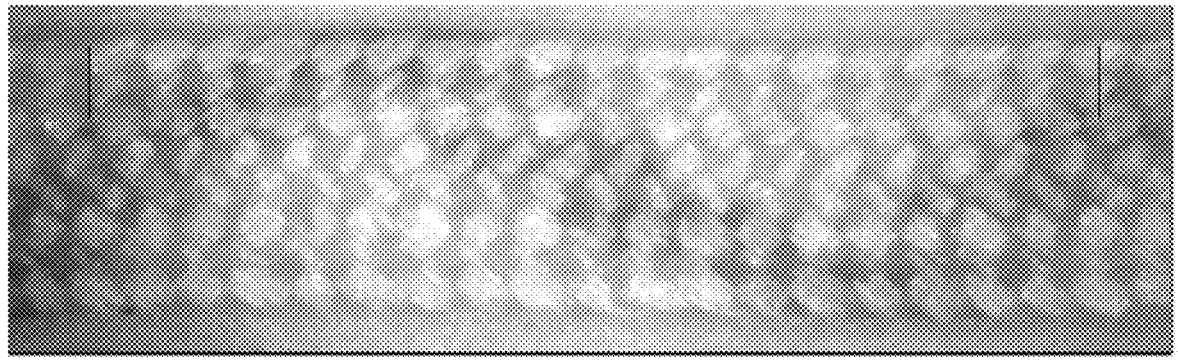
FIG. 6B illustrates another exemplary wave.

Focusing on the embodiments of FIGS. 6A and 6B, the markings along a filament, such as described above as to FIGS. 1 and 2B, can vary along at least one of the length and width of the filament. For example, the marking may not only extend along only a portion of the length of the filament, but may also only extend through a portion of the width of the filament. FIG. 6A illustrates an exemplary wave pattern extending along at least part of the length of the filament. Also, the wave pattern has a width that is less than the width of the filament, such that the wave pattern can undulate from one side of the filament to the other. In this manner, the wave pattern can "mark" on side of the filament along a portion of the length, and then "mark" the other side of the filament along another portion of the length, and further, can mark only the middle of the filament along yet another portion of the length. Of course, for each portion of the filament that is marked on one side, the other side is unmarked (or in the case of the marking being in the middle, neither side is marked). FIG. 6B illustrates another exemplary wave pattern, where the width of the wave also changes as it extends and undulates along the width of the filament as it extends along the length of the filament.

The marking in these examples of FIGS. 6A and 6B are due to the desired braiding pattern of the blue colored strands versus the other white colored strands. In yet another example, the wave pattern undulation could be used to denote length. For example, the wave pattern is positioned along a particular side of the filament every centimeter, such that the surgeon can easily determine the length of suture being used. As yet another example, the blue colored strands (or any color or colors desired) could also be braided such that the markings actually show a number or a letter on the filament, again denoting length or any other information desired (company name, intended use, an arrow showing direction of tension, or the like).

The higher pick count of such filaments of the present invention provides for a tighter braid such that the filament is stiffer and less likely to fold in half during tension. As used herein, "fold" means, unless otherwise used in context, a decreased width of a filament where the filament folds over itself across its width such that the entirety of the surface area of the filament, defined by its width, is not utilized. Such folding is illustrated, for example, in FIG. 2A versus a lack of folding in FIG. 2B, as discussed below. In other words, the tighter braid may help such filaments maintain their flat shape even when under longitudinal tension, such as when pulling on tissue, which is attached to the filament, to reduce an injury or the like. By maintaining the flat shape, the added surface area provided by the wider, flatter shape provides for an improved contact area on the underlying tissue and, if present, underlying bone. Further, maintaining the flat shape also distributes the forces applied by the filament onto the tissue which may provide for improved fixation, a better repair, and a decreased likelihood that the filament might tear through the tissue.

This stiffness, if incorporated in traditional sutures, would have the detriment of being overly stiff such that it would not be easily manipulated. For example, knot tying would be very difficult as the suture would not deform within the knot, and thus the knot would be likely to fail, or at least would likely have a larger profile. However, the thinner structure of the embodiment of FIGS. 1 and 2B, for example (as discussed above), decreases this detrimental side effect of a stiffer filament. Due to the thinner structure, even if the braid is stiff (by the high pick count), the flat morphology has a reduced moment of inertia in the direction the suture is bent, crushed or otherwise manipulated within the knot, and thus the resulting braided filament has a stiff braid that is easily manipulated (e.g., for knot tying, passing through tissue or instruments, etc.).

The results of this difference in pick count are illustrated in FIGS. 2A and 2B, illustrating two 1.9 mm suture tapes having different pick counts. Each of the suture tapes is illustrated as being under tension (as illustrated repairing a labrum tear). FIG. 2A illustrates a suture tape with a pick count of about 40, as known in the art. FIG. 2B, on the other hand, illustrates an example of the present invention—the filament of FIG. 2B has a pick count of about 80. As discussed above, the lower pick count suture tape (FIG. 2A), once under tension, has a narrower footprint than the higher pick count suture (FIG. 2B) which is also under tension. This narrower footprint is caused by the looser weave of the lower pick count suture, thereby allowing such a suture to fold over on itself.

Figure 3:
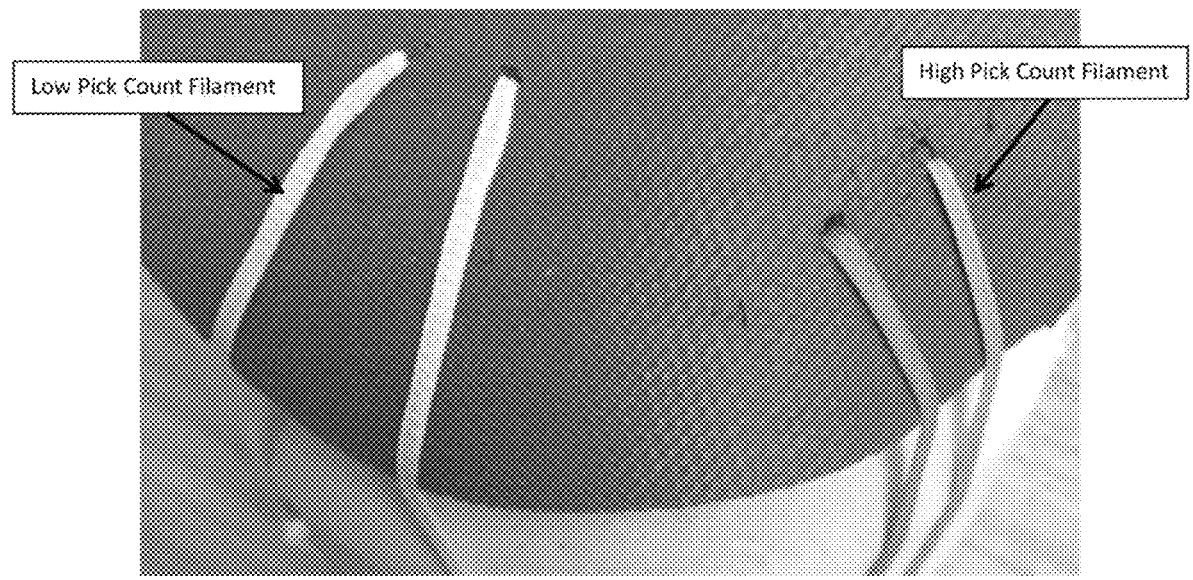
FIG. 3 illustrates a suture tape known in the art (a low pick count filament) and one embodiment of the present invention (a high pick count filament).

FIGS. 3-5 illustrate another example of how the higher pick count filament can better withstand longitudinal forces being applied thereto. FIG. 3 illustrates both the low pick count filament (pick count of about 35) and the high pick count filament (pick count of about 80), both under no tension—i.e., the filaments are simply lying over the "tissue" surface from nothing more than the force of gravity. The "tissue" in this example is a rubber flap commonly used in testing sutures and suture anchors.

Figures 4A, 4B:
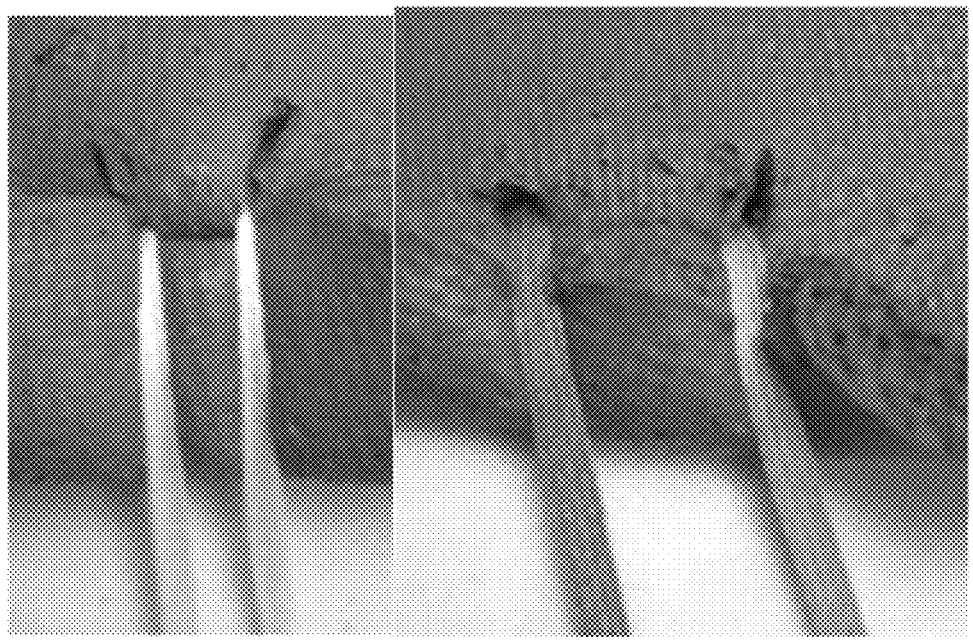
FIGS. 4A-4B and 5A-5B illustrate the filaments of FIG. 3 and the effect of various longitudinal forces being applied thereto.

Continuing with this example, FIG. 4A illustrates the low pick count filament under 4 Newtons of force, while FIG. 4B illustrates the high pick count filament under 4 Newtons of force. As illustrated, the low pick count filament is already folding in half, and thus, resulting in a decreased surface area against the tissue surface. The high pick count filament of FIG. 4B, on the other hand, maintains its flat shape over the tissue.

Figures 5A, 5B:
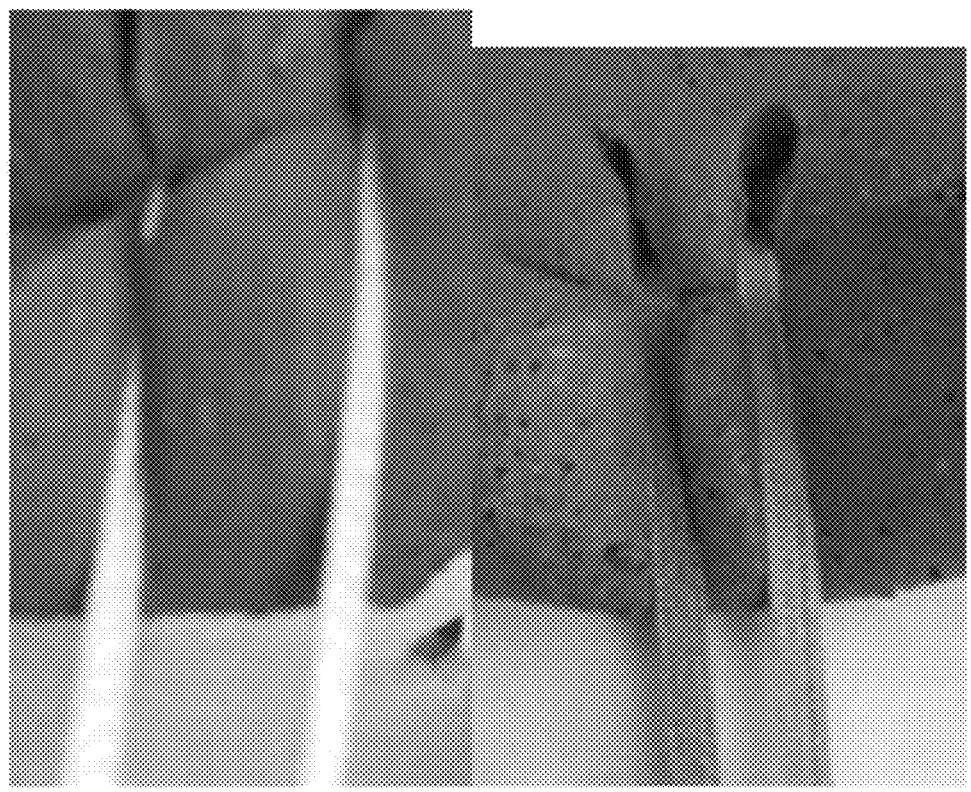

Further as to this example, FIG. 5A illustrates the low pick count filament under 15 Newtons of force. As illustrated, the filament has clearly folded over on itself and is resembling a round filament rather than a flat filament. FIG. 5B illustrates the high pick count filament under 35 Newtons. The high pick count filament is still maintaining its flat shape over the tissue, and thus, maintaining its wide footprint over the tissue.

Such forces of this example can be caused by the tension to the filament upon tying a knot or securing to a suture anchor, by any tissue compressed by the filament, and/or other such forces. While the higher pick count filament can maintain its shape despite these forces, a lower pick count filament folds over itself and thus destroys the benefits of its flat shape.

Another benefit of the higher pick count may help maintain the structural integrity of the suture during use. For example, traditional suture tape structures may pull apart, such as when the weave "opens" or "frays," during suture passing, shuttling, grabbing, or other such manipulation. A higher pick count suture tape has a smaller likelihood of pulling apart because of the tighter orientation of the fibers in the weave. In other words, there is less space in between fibers such that, when using an instrument, the instrument is likely to grab (or otherwise manipulate) the entirety of the suture tape rather than only grabbing a portion and creating spaces in between fibers. Similarly, in a situation where a portion of a higher pick count filament is pushed, or otherwise longitudinally compressed, such a filament may not "open up", again, due to the tighter braid pattern.

In another embodiment, the filament of the present invention may include at least a portion having a varying cross-section or shape different from the flat morphology. Examples of how such varying cross-sections are achieved are disclosed in U.S. Provisional App. No. 62/111,367, the entirety of which is incorporated by reference herein as if fully set forth herein.

In a further embodiment, the filament of the present invention may have an alternative shape other than the generally flat tape or sheet, discussed above. In this embodiment, the filament may instead have the cross-sectional shape of a flattened ellipse, or a double-thickness flat tape or filament. Such a filament may have a hollow interior or may alternatively be partially hollow, generally solid throughout, completely solid throughout, or the like. Preferably, the filament would be braided to have an annular shape with a hollow interior along at least a portion of its length, preferably its entire length. The hollow interior allows the filament to change its shape from an annular (e.g., round or elliptical) shape to a flattened shape, similar to the previous embodiment of the flat shape except rather than having a single layer, the resulting flat shape would have, for example, two layers. In other words, this filament may effectively compress or flatten to a double-thickness flat tape, which may, since it has twice the material, provide a filament with added strength and structural integrity. Alternatively, such a double-thickness tape can, even in a relaxed position, have a generally flat cross-section (rather than a more annular shape) such that the top flat portion of the tape generally contacts and lie on the bottom flat portion. Such a suture structure with a hollow interior may be useful in certain applications. For instance, the compressibility of such a hollow structure can be beneficial for knot-tying. In another example, the hollow structure can be useful for splicing, such as for tucking a portion of the tape through itself and into the hollow interior.

In one alternative to the compressible annular (e.g., round or elliptical) shape with a hollow interior, such a filament may also include an integrated core or a separate core positioned within the hollow interior of the filament. This core may provide added strength and structure to the filament, though it may decrease the compressibility of the filament into a flat shape, by virtue of the added material therein. Such a core may be separate from the annular filament or woven or otherwise integrated with the annular filament. In other embodiments, fiber(s) of the core may be integrated with the annular filament braiding such that the fiber(s) of the core can integrate with the exterior structure of the filament. Similarly, fiber(s) of the annular filament could integrate with the core or form a portion of the core. Other braiding variations are also envisioned.

Further, this integration of the core with the outer annular braiding may also provide an additional option for color or pattern markings. For example, at least one fiber of the core may have a color or marking different from the annular filament such that when such core fiber(s) is integrated and exposed on the annular filament, the color of the core fiber(s) would then be visible to a user. Thus, one or more fibers making up the core (or the single fiber making up the core) can alternate between being part of the annular filament, and thus be exposed on the exterior of the filament, and being the core, and thus be hidden inside the annular filament, such that any desired pattern can be created.

The filament of the present invention may be used in a variety of applications where a filament having a larger surface area would be beneficial.

For example, the filament of the present invention may be combined, either during manufacture or by a surgeon or other user, with at least one suture anchor, such as a knotless suture anchor and/or a filamentary suture anchor. One example of a filamentary suture anchor is the ICONIX® anchor (Stryker Corporation, San Jose, Calif.), as well as the anchor as illustrated in for example U.S. application Ser. Nos. 13/303,849 and 14/553,474, the entireties of which are incorporated by reference herein as if fully set forth herein. One example of a knotless anchor is the ReelX STT® Knotless Anchor System (Stryker Corporation, San Jose, Calif.).

In one embodiment, the filament may be used in rotator cuff repair where at least one suture anchor is used as a "medial" anchor and at least one suture anchor is used as a "lateral" anchor. In this repair, the flat filament extends from the medial anchor and over the tissue (forming the suture bridge) and into and through the lateral anchor. The filament is tensioned to compress the tissue to the underlying bone and the filament is secured in place. The larger surface area of the flat filament provides a larger footprint of compressive force against the tissue and bone, thereby improving the repair.

In another embodiment, the filament may be used in labrum repair in the hip or shoulder. Once again, the additional surface area of the flat filament may provide a larger compressive surface area against the labrum and underlying bone to improve the repair. Further, the use of the flat filament may also allow for fewer filament and suture anchor constructs to be used, thereby reducing the number of bone holes needed in the bone and number of suture passes through the tissue, thereby maintaining the integrity of more of the anatomy than if traditional round sutures were used.

In yet a further embodiment, the use of the flat filament in other repairs, such as the Achilles tendon, can provide similar benefits of a repair with increased surface area to promote increased compression of the repaired tissue. Uses of this filament in other areas of the anatomy are also envisioned.

As with any of these various repairs, maintaining the shape of the flat filament in its flat configuration is essential to ensuring the benefits are achieved. As such, the flat filament of the present invention, utilizing an increased pick count, may ensure that the flat surface area is fully utilized.

Various methods may be employed in preparing and manufacturing the above embodiments. Typically, and as described in the various embodiments below, a standard high-speed braiding machine, as well known in the art, is employed to form the woven filaments of the present invention. Typically such a braiding machine can utilize numerous fibers to form the braid. For example, employing such a braiding machine to create a standard round filament requires the use of an even number of fibers (e.g., 12, 14, 16) which are woven together by the braiding machine to form the round filament.

In one embodiment of the present invention, such a braiding machine is used to form a generally flat filament as illustrated for example in FIG. 1. To form the flat filament or filament tape, an odd number of fibers (e.g., 15 or 17) are woven together to form the flat shape. Further, the braiding machine can employ a roller or other mechanism which can further flatten the woven flat structure prior to being "taken up" or collected onto a bobbin or other collection mechanism. As discussed above, in certain embodiments of this manufacturing method, one or more of the fibers can have a contrasting color from the other fibers to form a marking pattern as desired.

In another embodiment, the present invention is a method of forming the double-thickness flat tape. In this embodiment, the braiding machine employs a large, even number of fibers to create a generally round filament. The filament may be hollow, substantially solid or completely solid. The hollow shape may allow for, for example, increased compression of the round filament to take on the double-thickness flat shape, and to provide a hollow interior for use in tucking or splicing of the filament.

Alternatively, the same method may be performed but with an odd number of fibers such that the resulting filament has an elliptical shape rather than a round shape. The elliptical shape may allow for easier compression of the filament into the flat shape as the distance of compression is limited to the minor diameter of the ellipse. As above, the hollow interior again allows for its use in tucking or splicing of the filament.

In another embodiment, the present invention is a method of forming the double-thickness flat tape or filament. In this embodiment, a double-wide substantially flat tape is formed, as discussed above. The double-side tape may require additional fibers to create the increased width, though, as above, an odd number of fibers is used. The tape may then be folded over itself in the lengthwise direction and the edges sewn together to form a tubular structure, which when compressed, creates the double-thickness flat filament as discussed above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

The invention claimed is:

1. A method of repairing tissue, comprising the steps of:
   accessing torn tissue to be repaired;
   inserting a braided filamentary device at least partially through the torn tissue, the braided filamentary device comprising a plurality of braided fibers forming the braided filamentary device having a substantially flat morphology defined by a length and a width;
   inserting a medial anchor and a lateral anchor into underlying bone; and
   applying a tensioning force along the length of the filamentary device such that the braided filamentary device compresses the torn tissue to the underlying bone, wherein the width of the braided filamentary device is substantially maintained under the tension.

2. The method of claim 1, further comprising the step of positioning the medial anchor in bone underneath the torn tissue to be repaired and positioning the lateral anchor in bone lateral of the torn tissue to be repaired such that the braided filamentary device extends from the medial anchor, through the torn tissue to be repaired, over the top of the torn tissue to be repaired, and to the lateral anchor, wherein the tensioning step tensions the braided filamentary device between the medial anchor and the lateral anchor to form a bridge over the torn tissue and compresses the torn tissue to the underlying bone.

3. The method of claim 1, wherein the step of applying the tensioning force applies a tension to the braided filamentary device of at least 10 Newtons.

4. The method of claim 1, wherein the torn tissue is a rotator cuff.

5. The method of claim 1, wherein the torn tissue is an Achilles tendon.

6. The method of claim 1, wherein the torn tissue is a labrum, hip or shoulder.

7. The method of claim 1, wherein the width of the braided filamentary device is between about 0.7 mm and about 3.0 mm.

8. The method of claim 7, wherein the width is about 1.2 mm.

9. The method of claim 7, wherein the width is about 1.9 mm.

10. The method of claim 1, wherein the braided filamentary device has a pick count of at least about 50 picks per inch.

11. The method of claim 10, wherein the pick count is between about 50 and about 100 picks per inch.

12. The method of claim 11, wherein the pick count is about 75 picks per inch.

13. The method of claim 1, wherein the braided filamentary device comprises a height of between about 0.2 mm and about 0.4 mm.

14. The device of claim 13, wherein the height is between about 0.28 mm and about 0.38 mm.

15. The method of claim 1, further comprising the step of selecting the length of the filamentary device.

16. The method of claim 15, wherein the braided filamentary device comprises at least one colored fiber that undulates back and forth from a first lateral side of the filamentary device to an opposite second lateral side of the filamentary device to incrementally mark distances along the length of the filamentary device.

17. The method of claim 16, wherein the step of selecting the length of the filamentary device comprises determining a cumulative distance of the incrementally marked distances.

18. The method of claim 1, wherein the braided filamentary device comprises an odd number of the plurality of braided fibers.

19. The method of claim 18, wherein the odd number of the plurality of braided fibers is 15 or 17.

20. A method of repairing tissue, comprising the steps of:
   accessing torn tissue to be repaired;
   inserting a braided filamentary device at least partially through the torn tissue, the braided filamentary device comprising a plurality of braided fibers forming the braided filamentary device having a substantially flat morphology defined by a length and a width, and having a pick count of at least about 50 picks per inch; and
   applying a tensioning force along the length of the filamentary device such that the braided filamentary device compresses the torn tissue to underlying bone, wherein the width of the braided filamentary device is substantially maintained under the tension.

* * * * *